United States Patent
Gildersleeve

(10) Patent No.: US 12,102,549 B2
(45) Date of Patent: Oct. 1, 2024

(54) SMART BRACE AND HINGE ASSEMBLIES FOR SAME

(71) Applicant: DJO, LLC, Vista, CA (US)

(72) Inventor: Richard E. Gildersleeve, Carlsbad, CA (US)

(73) Assignee: DJO, LLC, Carlsbad, CA (US)

( * ) Notice: Subject to any disclaimer, the term of this patent is extended or adjusted under 35 U.S.C. 154(b) by 143 days.

(21) Appl. No.: 17/154,858

(22) Filed: Jan. 21, 2021

(65) Prior Publication Data

US 2021/0220160 A1 Jul. 22, 2021

Related U.S. Application Data

(60) Provisional application No. 62/964,325, filed on Jan. 22, 2020.

(51) Int. Cl.
*A61F 5/01* (2006.01)

(52) U.S. Cl.
CPC .... *A61F 5/0125* (2013.01); *A61F 2005/0139* (2013.01); *A61F 2005/0144* (2013.01)

(58) Field of Classification Search
CPC ........ A61F 5/0125; A61F 5/01; A61F 5/0123; A61F 5/00; A61F 5/0102; A61F 2005/0139; A61F 2005/0144; A61F 2005/0132; A61F 2005/0167; A61F 5/0109; A61F 5/0118; A61F 5/0127; A61F 5/013; A61F 5/0585; A61F 5/05858; A61F 2005/0146; A61B 5/11; A61B 5/00; A61B 5/107; A61B 5/1121; A61B 5/1073; A61B 5/4533; A61B 5/112; A61B 5/4585; A61H 1/00;
(Continued)

(56) References Cited

U.S. PATENT DOCUMENTS 4,805,606 A * 2/1989 McDavid, III ........ A61F 5/0125 2/22
4,986,263 A * 1/1991 Dickerson ............. A61F 5/0109 2/24

(Continued)

FOREIGN PATENT DOCUMENTS

EP 1 229 874 8/2002

OTHER PUBLICATIONS

Ellsworth, Nov. 24, 2015, Smart Brace, ECE 498: Capstone Design Project, 38 pp.

(Continued)

*Primary Examiner* — Alireza Nia
*Assistant Examiner* — Daniel A Miller
(74) *Attorney, Agent, or Firm* — KNOBBE, MARTENS, OLSON & BEAR LLP

(57) ABSTRACT

A smart brace is configured to be worn on a limb over the joint and includes a sensor that gathers data related to motion. The sensor can be included in a hinge assembly of the smart brace. The hinge assembly can include a first gear and a first bar and a second gear and a second bar. The first gear can be meshingly engaged with the second gear such that rotation of one causes corresponding rotation of the other. The first bar and the second bar are configured in size and shape to be flexible in a frontal plane and rigid in a sagittal plane. An end of the first bar and an end of the second bar can be received within corresponding recesses of the first gear and the second gear.

14 Claims, 14 Drawing Sheets

(58) Field of Classification Search
CPC .... A61H 1/0237; A61H 1/024; A61H 1/0244; A61H 1/0255; A61H 2003/007; E05D 7/12; E05D 2007/128
USPC .......................................... 602/16, 26, 5, 23
See application file for complete search history.

(56) References Cited

U.S. PATENT DOCUMENTS

| | | |
|---|---|---|
| 6,402,711 B1 | 6/2002 | Nauert |
| 6,527,733 B1 | 3/2003 | Ceriani et al. |
| 6,623,439 B2 | 9/2003 | Nelson et al. |
| 9,351,864 B2 | 5/2016 | Romo et al. |
| 9,668,903 B2 | 6/2017 | Hsu et al. |
| 9,788,986 B2 | 10/2017 | Dunn |
| 2003/0149386 A1* | 8/2003 | Ceriani ................. A61F 5/0123 602/26 |
| 2005/0038367 A1 | 2/2005 | McCormick et al. |
| 2006/0155229 A1* | 7/2006 | Ceriani ................. A61F 5/0125 602/5 |
| 2006/0200057 A1 | 9/2006 | Sterling |
| 2009/0118656 A1* | 5/2009 | Ingimundarson ..... A61F 5/0123 602/26 |
| 2011/0152736 A1* | 6/2011 | Ng ........................ A61F 5/0123 602/16 |
| 2014/0163444 A1 | 6/2014 | Ingvarsson |
| 2014/0303534 A1 | 10/2014 | Huffa et al. |
| 2015/0057587 A1 | 2/2015 | Walsh et al. |
| 2017/0086671 A1 | 3/2017 | Sessler |
| 2017/0367867 A1* | 12/2017 | Nathanson ............ A61F 5/0123 |
| 2019/0133497 A1* | 5/2019 | Moore ................... A61B 5/1121 |
| 2019/0159919 A1* | 5/2019 | Turconi ................ A61F 5/0102 |

OTHER PUBLICATIONS

International Search Report and Written Opinion dated Jul. 27, 2021 in application No. PCT/US2021/014437.

\* cited by examiner

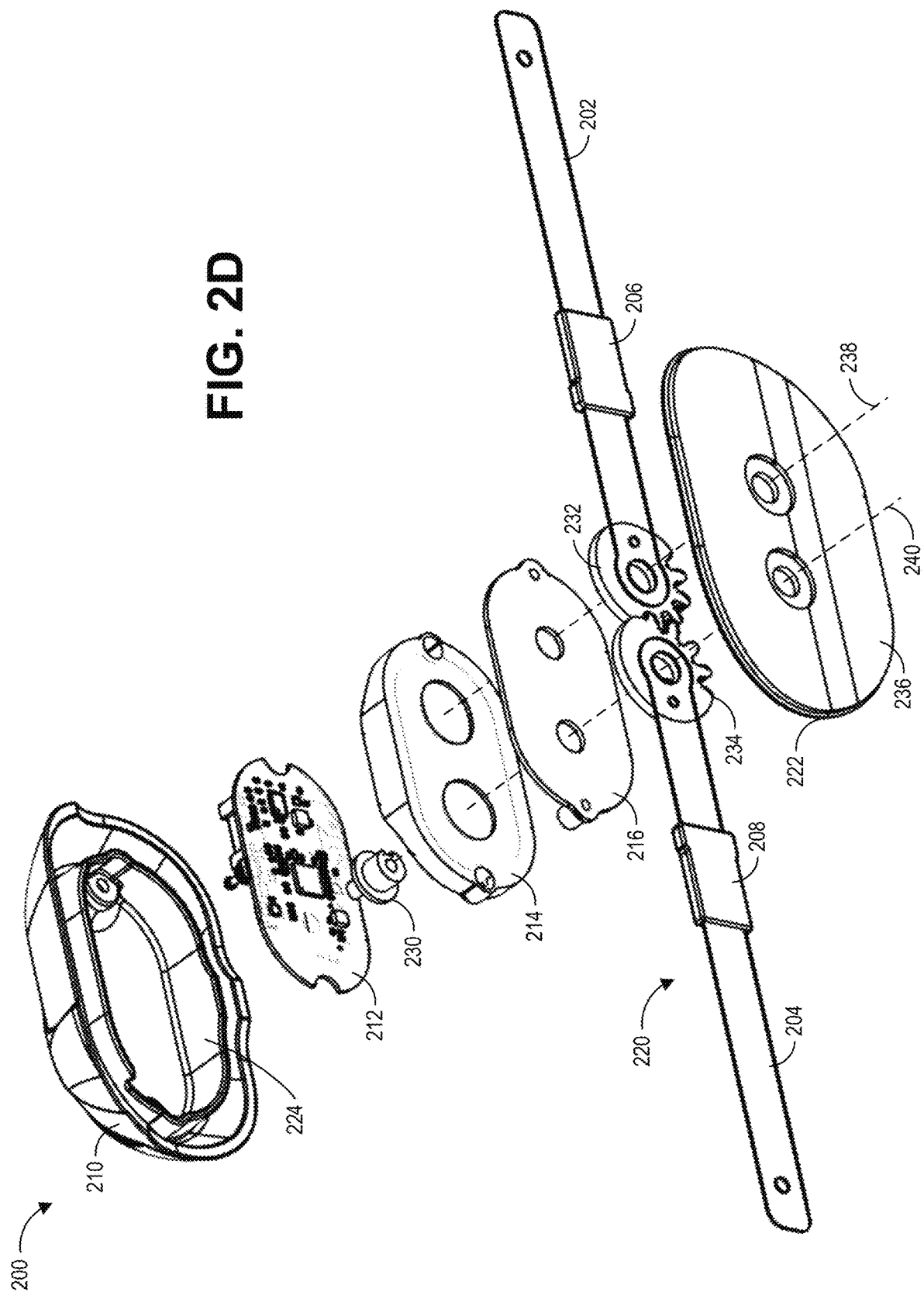

SMART BRACE AND HINGE ASSEMBLIES FOR SAME

PRIORITY APPLICATION

This application claims priority to U.S. Provisional Application No. 62/964,325, filed Jan. 22, 2020, which is incorporated by reference herein. Any and all applications for which a foreign or domestic priority claim is identified in the Application Data Sheet as filed with the present application are hereby incorporated by reference under 37 CFR 1.57.

BACKGROUND

This application relates to braces and hinge assemblies for braces. In particular, this application relates to smart braces and hinge assemblies for the same that can be configured to gather data related to the motion of the limb and/or joint on which the smart brace is worn.

Orthopedic braces are medical apparatus that are generally externally applied to a limb, joint, or other body part to provide support for, strengthen, limit motion of, or provide other functionality for the limb, joint, or body part.

SUMMARY

Certain aspects of the disclosure will now be summarized. These and other aspects of the disclosure will become apparent from the following detailed description, drawings, and appended claims. This summary should not be construed as limiting the disclosure.

In a first aspect, a smart brace includes a flexible compressive garment configured to be worn on a limb over a joint and a smart hinge removably coupled to the garment. The smart hinge can include a first bar coupled to an upper portion of the garment above the joint, the first bar configured to rotate about a first axis with flexion or extension of the joint; a second bar coupled to a lower portion of the garment below the joint, the second bar configured to rotate about a second axis with flexion or extension of the joint; and at least one sensor configured to gather data related to motion of the joint. The first bar and the second bar are flexible in a frontal plane and rigid in a sagittal plane.

The smart brace may include one or more of the following features in any combination: (a) wherein each of the first bar and the second bar comprise a thickness less than or equal to about 1.0 mm, less than or equal to about 0.75, or less than or equal to about 0.5 mm providing flexibility in the frontal plane, and a width greater than or equal to about 5.0 mm, greater than or equal to about 7.5 mm, or greater than or equal to about 10 mm providing rigidity in the sagittal plane; (b) wherein each of the first bar and the second bar comprise spring steel; (c) wherein a first end of the first bar is countersunk within a first gear, and a first end of the second bar is countersunk within a second gear, the second gear meshingly engaged with the first gear such that rotation of the first bar about the first axis causes a corresponding rotation of the second bar about the second axis; (d) wherein the garment comprises an upper receptacle fixedly attached to the upper portion of the garment, the upper receptacle comprising a slot that removably receives a second end of the first bar to couple the first bar to the upper portion, and a lower receptacle fixedly attached to the lower portion of the garment, the lower receptacle comprising a slot that removably receives a second end of the second bar to couple the second bar to the second portion; (e) wherein the first bar comprises a first insert overmolded on the first bar between the first end and the second end, the first insert configured to engage with the slot of the upper receptacle, and the second bar comprises a second insert overmolded on the second bar between the first end and the second end, the second insert configured to engage with the slot of the lower receptacle; (f) wherein the smart hinge assembly is coupled to the garment on a lateral side, and the smart brace further comprises a dummy hinge assembly coupled to the garment on the medial side; (g) wherein the dummy hinge assembly comprises a first bar coupled to an upper portion of the garment above the joint, the first bar configured to rotate about a first axis with flexion or extension of the joint, and a second bar coupled to a lower portion of the garment below the joint, the second bar configured to rotate about a second axis with flexion or extension of the joint, wherein the first bar and the second bar are flexible in a frontal plane and rigid in a sagittal; and/or (h) wherein the joint comprises a knee.

In another aspect, a hinge assembly for a smart brace is described, the hinge assembly comprising: a first geared arm assembly comprising a first gear and a first bar, an end of the first bar received within a recess of the first gear; a second geared arm assembly comprising a second gear and a second bar, an end of the second bar received within a recess of the second gear; and a hinge plate, the first geared arm assembly connected to the hinge plate for rotation about a first axis and the second geared arm assembly connected to the hinge plate for rotation about a second axis, and the first gear meshingly engaged with the second gear such that rotation of the first geared arm assembly causes a corresponding rotation of the second geared arm assembly. The first bar and the second bar are flexible in a frontal plane and rigid in a sagittal plane.

The hinge assembly may include one or more of the following features, in any combination: (a) wherein each of the first bar and the second bar comprise a thickness less than or equal to about 1 mm providing flexibility in the frontal plane, and a width greater than or equal to about 5 mm providing rigidity in the sagittal plane; (b) wherein each of the first bar and the second bar comprise a thickness less than or equal to about 0.75 mm providing flexibility in the frontal plane, and a width greater than or equal to about 7.5 mm providing rigidity in the sagittal plane; (c) wherein each of the first bar and the second bar comprise a thickness less than or equal to about 0.5 mm providing flexibility in the frontal plane, and a width greater than or equal to about 10 mm providing rigidity in the sagittal plane; (d) wherein each of the first bar and the second bar comprise spring steel; (e) wherein the recess of each of the first and second gears comprises a shape that corresponds to a shape of the end of the corresponding first and second bars, such that the end of each of the first and second bars is closely received within the corresponding recess of the first and second gears; (f) wherein the recess of each of the first and second gears is configured such that the corresponding first and second bars is countersunk within the corresponding recess of the first and second gears; (g) at least one sensor configured to gather data related to motion of at least one of the first and second geared arm assemblies, and a power source electrically coupled to the at least one sensor; (h) wherein the at least one sensor comprises a potentiometer, the end of one of the first bar or the second bar comprises a keyed opening, and a drive key engaged with the keyed opening couples the potentiometer to the end of the one of the first bar or the second bar such that rotation of the one of the first bar or the second bar about the corresponding first or second axis adjusts an output of the potentiometer; (i) wherein the at least one sensor and the power source are positioned on a printed circuit board, and the hinge assembly further comprises a gasket that at least partially receives the printed circuit board, and a cover that covers the gasket and the printed circuit board, wherein the gasket and cover define a water resistant recess in which the printed circuit board is positioned; and/or (j) wherein the hinge plate, the gasket, the printed circuit board, and the cover are positioned on a first side of the first and second geared arms, a condyle is positioned on a second side of the first and second geared arms, and during use of a smart brace including the hinge assembly, the first side is positioned away from a wearer and the second side is positioned toward the wearer.

BRIEF DESCRIPTION OF THE DRAWINGS

The features and advantages of the smart brace and hinge assemblies described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

FIG. 2D is a second exploded perspective view of the smart hinge assembly.

DETAILED DESCRIPTION

Figure 1:
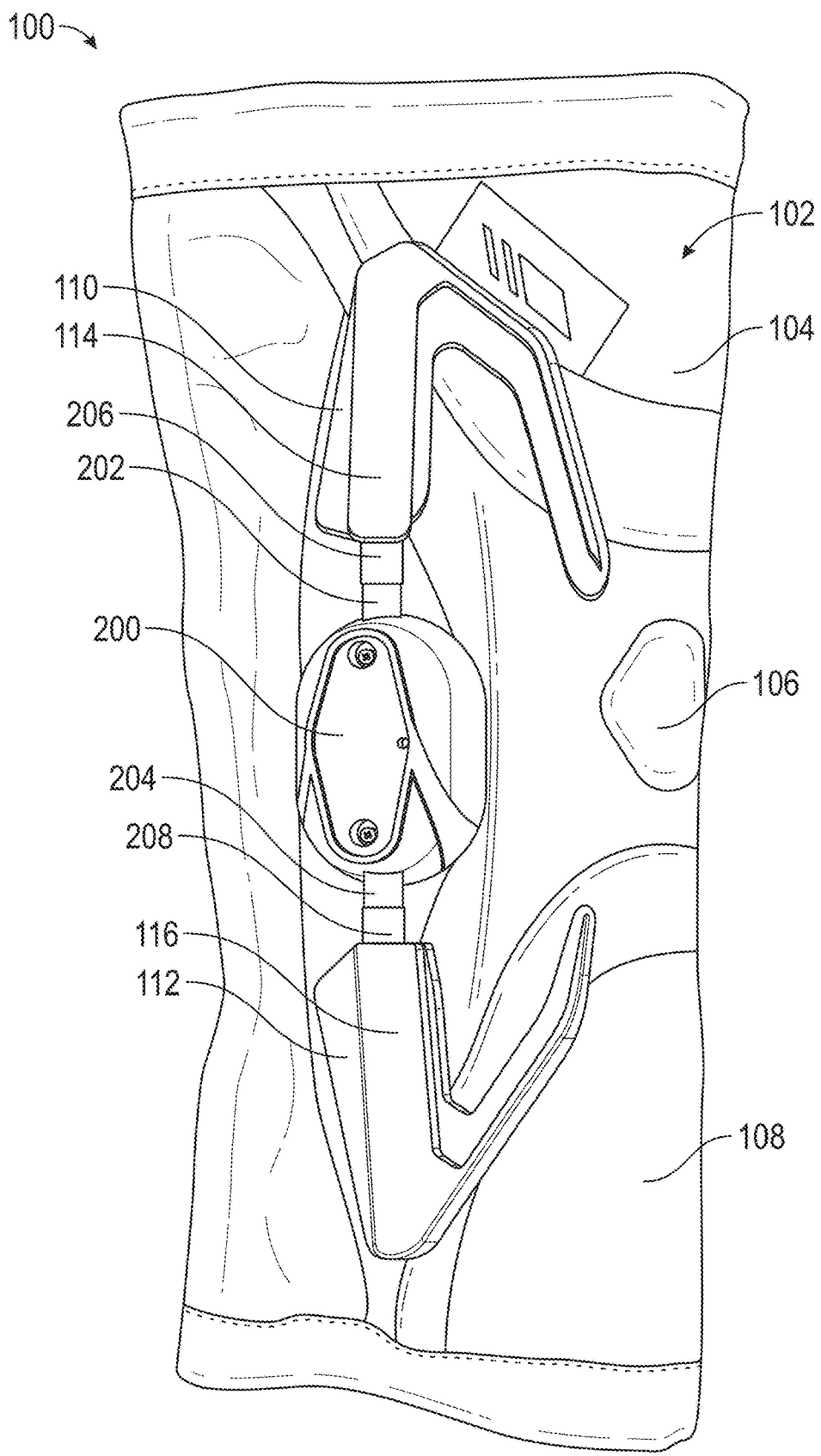
FIG. 1 illustrates a lateral view of an embodiment of a smart brace including an embodiment of a smart hinge assembly.

The following discussion presents detailed descriptions of the several embodiments of a smart brace and hinge assemblies for the same as shown in the figures. Although several embodiments, examples, and illustrations are disclosed below, it will be understood by those of ordinary skill in the art that the inventions described herein extend beyond the specifically disclosed embodiments, examples, and illustrations and include other uses of the inventions and obvious modifications and equivalents thereof. The terminology used in the description presented herein is not intended to be interpreted in any limited or restrictive manner simply because it is being used in conjunction with a detailed description of certain specific embodiments. In addition, embodiments of the inventions can comprise several novel features and no single feature is solely responsible for its desirable attributes or is essential to practicing the inventions herein described.

Various embodiments disclosed herein relate to smart braces and hinge assemblies for the same. The smart braces can be configured to collect data related to the motion of the limb and/or joint on which the brace is worn. For example, the smart braces can include various types of sensor technology from which the data related to the motion of the limb and/or joint can be measured or otherwise determined. In some embodiments, the sensor technology is incorporated into a hinge assembly of the smart brace. In such instances, the hinge assembly can be considered a smart hinge assembly.

In some, but not all, embodiments, the smart braces can be configured such that the primary function or purpose of the smart braces is to collect the data related to the motion of the limb and/or joint. That is, unlike many braces whose primary purposes are directed to providing additional structural strength for a joint or limiting motion of the joint, in some embodiments, the primary purpose of the smart braces described herein is primarily directed towards data gathering. As such, many of the smart braces described herein are configured to provide excellent fit and comfort, while maintaining the ability to accurately gather the data related to the motion of the limb and/or joint. In some embodiments, the smart braces can be configured to provide support and/or compression to the limb and/or joint on which they are worn.

In some embodiments, the hinge assemblies for the smart braces described herein can be configured such that the overall thickness thereof is reduced. Such hinge assemblies can be considered low profile. In some embodiments, such low profile hinge assemblies can maintain their low profile while including the sensor technologies for gathering data related to the motion of the limb and/or joint.

In some embodiments, the hinge assemblies for smart braces described herein (whether smart or otherwise) can be configured to (1) provide excellent fit and comfort while maintaining the ability to collect accurate data related to the motion of the limb and/or joint, and/or (2) maintain a low profile by including one or more of the following features:

Bars that are very flexible in a frontal plane so as to provide body conforming, comfort, and/or a low profile, while being very stiff in a sagittal plane so as to provide accurate data related to the motion of the limb and/or joint. Such bars can be, for example, about 0.5 mm thick (to provide flexibility in the frontal plane) and about 10 mm wide (to provide stiffness in the sagittal plane). Such bars can be made from spring steel, for example. Other dimensions and materials as described in more detail below are also possible.

Ends of the bars can be countersunk within recesses of corresponding gears. Countersinking the ends of the bars within the corresponding gears can minimize the overall thickness of the hinge, providing a low profile, and/or facilitate a rigid connection between the bars and the gears, facilitating overall stiffness in the sagittal plane.

The smart braces and hinge assemblies described herein can be used in a variety of contexts. In one example, the smart braces are useful during a recovery phase after a medical procedure. For example, during an ACL recovery phase it can desirable to have a low profile hinge that allows the clinician and patient to gather data related to the motion of the knee to quantify recovery information progress in a non-burdensome low-profile manner. In some embodiments, the smart braces are useful in applications wherein a high degree of medial-lateral support is not required.

Although the primary example described throughout this application relates to a recovery knee brace, the smart braces and hinge assemblies described herein can also be used or modified for use in other types of braces, such as elbow braces or others, as well as in other contexts.

FIG. 1 illustrates a lateral view of an embodiment of a smart brace 100 including an embodiment of a smart hinge assembly 200. The smart hinge assembly 200 may include at least one sensor configured to gather data related to the motion of joint and/or limb on which the smart brace 100 is worn. A detailed example embodiment of the smart hinge assembly 200 is presented in FIGS. 2A-4B, which are described below. A medial view of the smart brace 100 may appear similar to the lateral view shown in FIG. 1 and may include another hinge assembly on the medial side of the smart brace 100. The hinge assembly on the medial side of the smart brace 100 may comprise a smart hinge assembly including at least one sensor, or it may comprise a hinge assembly that does not include a sensor (referred to herein as a dummy hinge assembly or non-smart hinge assembly). An example of such a dummy hinge assembly 300 is provided in FIGS. 5A-5D, which are described below.

In the illustrated embodiment, the smart brace 100 is configured for use on a user's knee. However, while the illustrated embodiment is described in relation to the user's knee, the smart brace 100 may be modified for use on other joints, such as, for example, elbows, ankles, or others. The smart brace 100 may be configured for use on either a right knee or left knee of the user. In some embodiments, the smart brace 100 is configured such that the smart hinge assembly 200 is positioned on a lateral side of the user's knee and the dummy hinge assembly is positioned on a medial side of the user's knee. In some embodiments, the dummy hinge assembly can be omitted, and the smart hinge assembly 200 can be positioned on the lateral side or the medial side of the user's knee.

The smart brace 100 can be configured as a recovery brace. For example, in some embodiments, the smart brace 100 is intended to be used during a recovery phase after an injury or medical procedure. The smart brace 100 can gather data related to the motion of the knee that can be assessed to quantify recovery. As noted above, in some embodiments, a primary purpose of the smart brace 100 is to gather such data. Accordingly, in some embodiments, the smart brace 100 provides limited or no support for the knee. The smart brace 100 can be configured to be low-profile and comfortable such that it can be worn without restricting movement of the knee. In some embodiments, the smart brace 100 is configured to provide compression or compressive support for the knee. In some embodiments, the smart brace 100 can include structural components or framing to provide significant support for the knee.

In the illustrated embodiment, the smart brace 100 includes a garment 102 and the smart hinge assembly 200. The garment 102 is configured to be worn on the user's leg over the knee joint. The garment 102 is further configured to support and position the smart hinge assembly 200 and the dummy hinge assembly (if included). In the illustrated embodiment, the garment 102 comprises a sleeve. The sleeve may comprise a continuous loop of material configured to be worn on the leg over the knee. The sleeve may comprise a flexible, elastic material such that a tight or compressive fit is provided by the sleeve. Other embodiments for the garment 102 are also possible. For example, the garment 102 may comprise a wrap configured to be wrapped around the leg over the knee and secured by one or more fasteners. The wrap may comprise a flexible material, which may or may not be elastic. The fasteners can include one or more straps, laces, buckles, or other types of fasteners.

As shown in FIG. 1, the garment 102 includes an upper portion 104, a central portion 106, and a lower portion 108. The upper portion 104 is configured to engage with a portion of the user's leg above the knee joint. The central portion 106 is configured to engage with the user's leg around the knee joint. The lower portion 108 is configured to engage with the user's leg below the knee joint.

With continued reference to the illustrated embodiment of FIG. 1, an upper receptacle 110 is provided on the upper portion 104 and a lower receptacle 112 is provided on the lower portion 108. The upper receptacle 110 can be fixedly attached to the upper portion 104 and the lower receptacle 112 can be fixedly attached to the lower portion 108. For example, in some embodiments, the upper receptacle 110 is molded onto (e.g., injection molded onto) the upper portion 104 and the lower receptacle 112 is molded onto the lower portion 108. The upper and lower receptacles 110, 112 may comprise a rigid or semi-rigid material. In some embodiments, the upper and lower receptacles 110, 112, comprise silicone, although other similar and suitable materials may be used.

The upper and lower receptacles 110, 112 may be configured to allow the smart hinge assembly 200 to be coupled to the garment 102. In some embodiments, the upper and lower receptacles 110, 112 may be configured to allow the smart assembly hinge 200 to be removably coupled to the garment 102. Removably coupling the smart hinge assembly 200 to the garment 102 can allow the smart hinge assembly 200 to be removed from the garment to allow the garment 102 to be used without the smart hinge assembly 200, to allow the smart hinge assembly 200 to be replaced if necessary, and/or during cleaning of washing of the garment 102. In the illustrated embodiment, the upper receptacle 110 comprises an upper slot 114 formed therein and the lower receptacle 112 comprise a lower slot 116 formed therein.

The upper slot 114 can be configured to receive a first or upper bar 202 of the smart hinge assembly 200. For example, one end of the upper bar 202 can be slid into the upper slot 114. Engagement of the upper bar 202 and the upper slot 114 can couple the upper bar 202 to movement of the portion of the user's leg above the knee. Similarly, the lower slot 116 can be configured to receive a second or lower bar 204 of the smart hinge assembly 200. For example, one end of the lower bar 204 can be slid into the lower slot 116. Engagement of the lower bar 204 and the lower slot 116 can couple the lower bar 204 to movement of the portion of the user's leg below the knee. In this way, motion (e.g., extension or flexion) of the user's knee causes a corresponding movement of the upper and lower bars 202, 204. The at least one sensor within the smart hinge assembly 200 can be configured to gather data related to this motion.

As shown in FIG. 1 and described in more detail below, in some embodiments, an insert 206 can be provided on the upper bar 202. In some embodiments, the insert 206 comprises an elastomer or other material overmolded onto the upper bar 202 in a region at which the upper bar 202 enters the upper slot 114. The insert 206 can be configured in size and shape to provide various functionality. For example, the insert 206 can be configured to locate the upper bar 202 within the upper slot 114 and provide a tight fit therebetween. The insert 206 can also be configured to distribute contact forces between the upper bar and the upper slot 114 over a larger surface area to reduce or prevent wear between the upper bar 202 and the upper slot 114. The insert 206 can also be configured elevate the upper bar 202 slightly above the fabric of the garment 102 to prevent the upper bar 202 from cutting or puncturing the garment 102. A similar insert 208 can be provided on the lower bar 204 and configured to provide similar functionality with respect to the lower bar 202 and the lower slot 116.

Although not illustrated in FIG. 1, similar upper and lower receptacles may be provided on the medial side of the brace for engaging with a medial hinge assembly, if present.

Figure 2A:
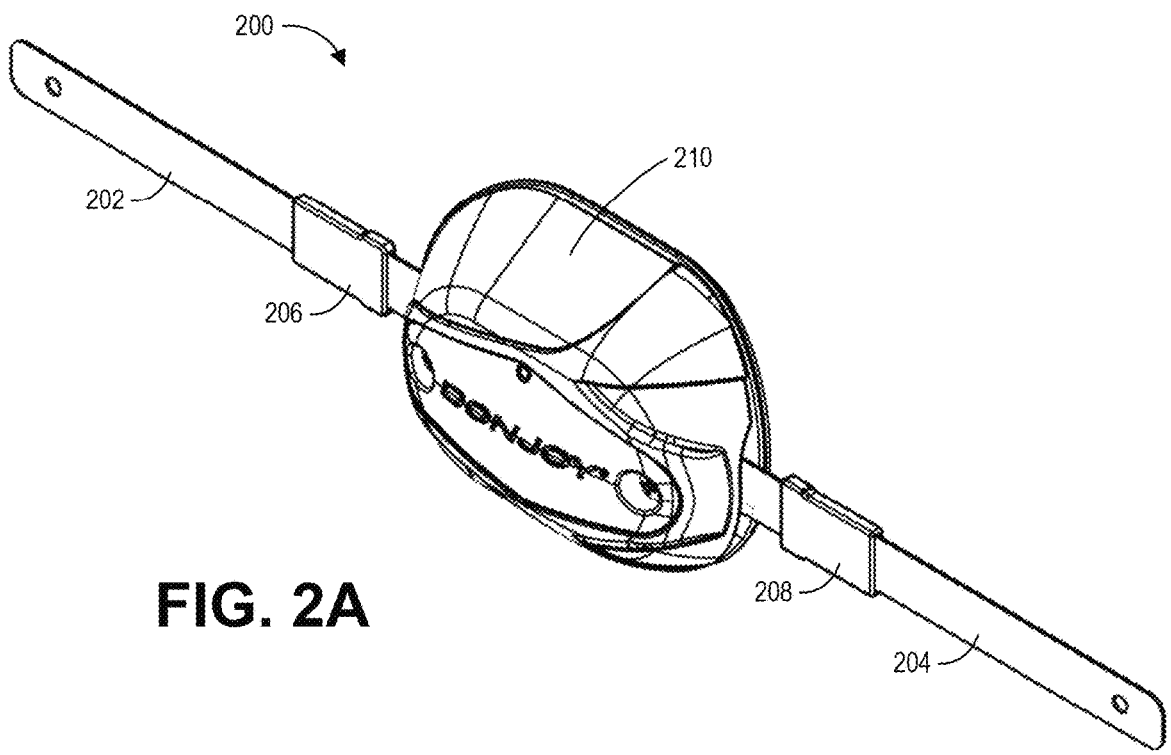
FIG. 2A is a perspective view of a first side of the smart hinge assembly of FIG. 1.
Figure 2B:
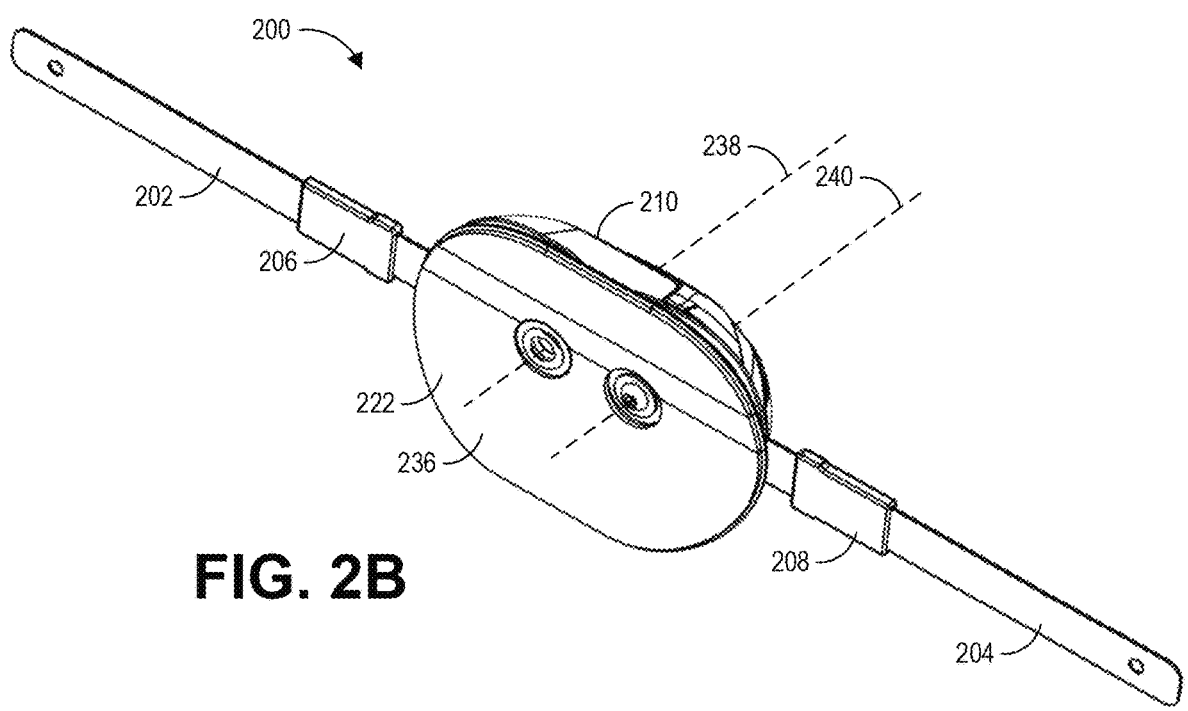
FIG. 2B is a perspective view of a second side of the smart hinge assembly.
Figure 2C:
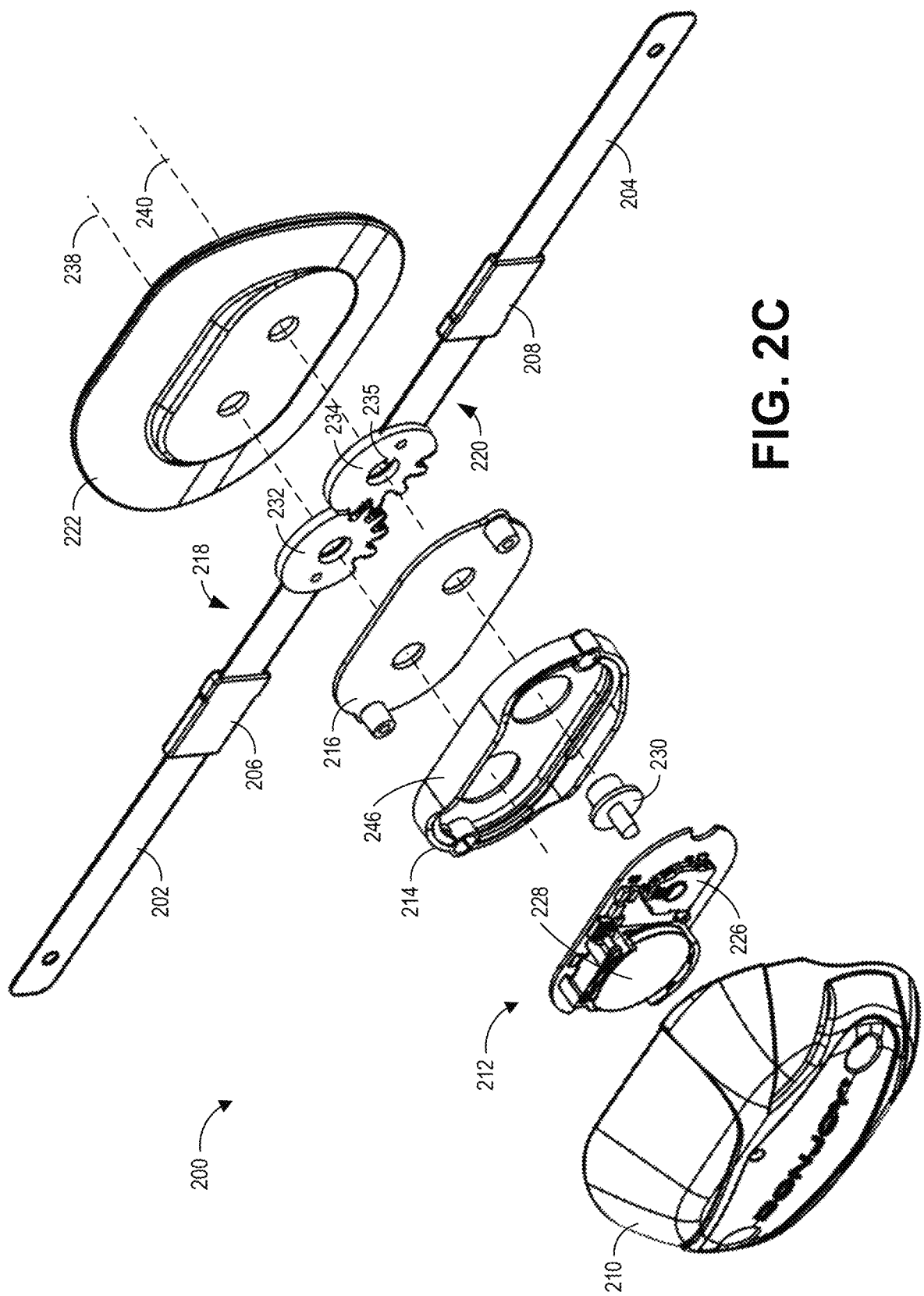
FIG. 2C is a first exploded perspective view of the smart hinge assembly.
Figure 2E:
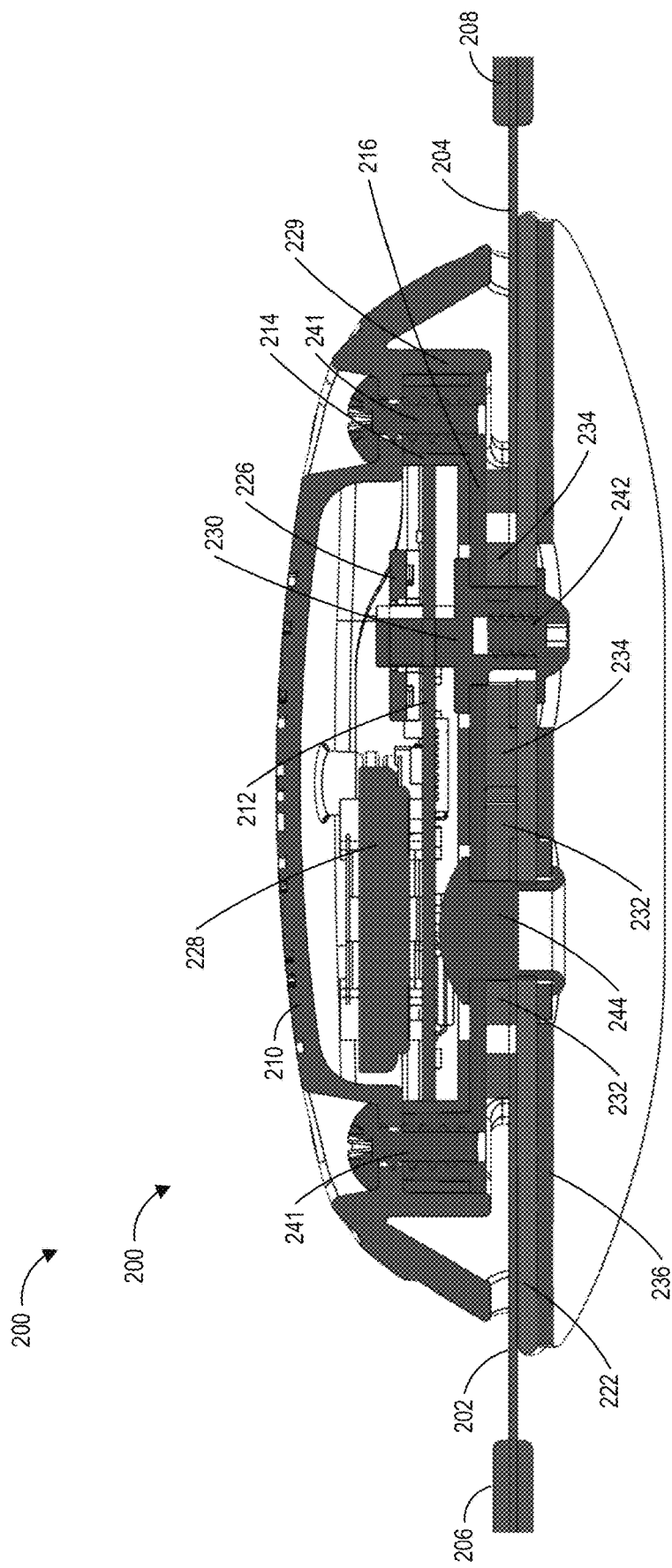
FIG. 2E is a cross-sectional view of the smart hinge assembly taken through a sagittal plane.

FIGS. 2A-2E illustrate an embodiment of the smart hinge assembly 200 in greater detail. In particular, FIGS. 2A and 2B are first and second perspective views of the smart hinge assembly 200, FIGS. 2C and 2D are first and second exploded views of the smart hinge assembly 200, and FIG. 2E is a cross-sectional view of the smart hinge assembly 200 taken through a sagittal plane. As best seen in the first and second exploded views of FIGS. 2C and 2D, in the illustrated embodiment, the smart hinge assembly 200 comprises a cover 210, a printed circuit board (PCB) 212, a gasket 214, a hinge plate 216, a first or upper geared arm assembly 218, a second or lower geared arm assembly 220, and a condyle 222, each of which are described in more detail below.

FIG. 2A illustrates a first perspective view of the smart hinge assembly 200 showing an outer side thereof. During use, the outer side of the smart hinge assembly 200 is configured to face away from the user's body. As shown in FIG. 2A, the upper and lower bars 202, 204 extend outwardly from beneath the cover 210. As will be described in more detail below, the cover 210 is configured to cover and enclose various internal components of the smart hinge assembly 200. Within the cover 210, ends of the first and second bars 202, 204 are pivotally coupled to the smart hinge assembly 200 such that the first and second bars 202, 204 can rotate with respect to the cover 210 about a first axis 238 and a second axis 240, respectively. The first and second axes 238, 240 are illustrated in FIGS. 2B-2D.

FIG. 2B is a second perspective view of the smart hinge assembly 200 showing an inner side thereof. During use, the inner side of the smart hinge assembly 200 is configured to face towards the user's body. In some embodiments, the inner side of the smart hinge assembly 200 contacts the garment 102 or the user's body. As shown in FIG. 2B, on the inner side, the smart hinge assembly 200 comprises a condyle plate or structure 222 (referred to herein as condyle 222). The condyle 222 can be configured in size and shape to generally correspond to the portion of the user's body that the inner side of the smart hinge assembly 200 contacts. For example, when the smart hinge assembly 200 is configured for use on the medial side of the user's knee, the condyle 222 can be configured with a shape that generally corresponds to the shape of the medial side of the user's knee (e.g., the condyle 222 can be curved to follow the contour(s) of the outer surface of the medial side of the user's knee).

In some embodiments, a condyle pad 236 is mounted on the surface of the condyle 222 that contacts the user's body or the garment 102. The condyle pad 222 may comprise a foam or other cushioning layer that is configured to improve the comfort of the smart hinge assembly 200 and smart brace 100. In some embodiments in which the smart hinge assembly 200 is configured such that the condyle 222 overlies the garment 102, the condyle pad 236 may comprise a fastener configured to attach the condyle 222 to the garment 102. For example, the condyle pad 236 may comprise a layer of hook or loop fastener configured to releasably engage with a corresponding layer of hook or loop fastener positioned on and attached to the garment 102.

FIG. 2B also illustrates that the upper and lower bars 202, 204 extend outwardly from the smart hinge assembly 200 at a position between the condyle 222 and the cover 210. FIG. 2B also illustrates example locations for the first and second axes 238, 240 about which the first and second bars 202, 204 are configured to pivot or rotate, respectively.

With reference now to the exploded perspective views of FIGS. 2C and 2D, additional components and structure, including internal components and structure, of the smart hinge assembly 200 will now be described. FIG. 2C is an exploded perspective view from the outer side of the smart hinge assembly 200 and FIG. 2D is an exploded perspective view from the inner side of the smart hinge assembly 200. In particular, FIGS. 2C and 3D illustrate the cover 210, the printed circuit board (PCB) 212, the gasket 214, the hinge plate 216, the first or upper geared arm assembly 218, the second or lower geared arm assembly 220, and the condyle 222 of the smart hinge assembly 200.

As noted previously, the smart hinge assembly 200 includes one or more sensors configured to gather data related to motion of the limb or joint on which the smart brace 100 including the smart hinge assembly 200 is worn. As shown in FIGS. 2C and 2D, in the illustrated embodiment, the one or more sensors are included on the PCB 212, along with a power source 228, and other electronic components. In the illustrated embodiment, the one or more sensors comprise a potentiometer 226 mounted on the PCB 212. The potentiometer 226 includes a rotatable component that can be actuated to adjust an output (e.g., an output voltage) of the potentiometer 226. As will be described in more detail below, the rotatable component of the potentiometer 226 is rotationally coupled to one of the first or second bars 202, 204 by way of a drive key 230. In the illustrated embodiment, the drive key 230 couples the rotatable component of the potentiometer 226 to the second bar 204. Accordingly, as the second bar 204 rotates (as caused by flexion or extension of the knee), the rotation is transferred by way of the drive key 230 to the rotatable component of the potentiometer 226, adjusting the output thereof. The output of the potentiometer 226 can then be used to determine information related to the motion of the knee.

In addition to or in place of the potentiometer 226, one or more additional sensors can be included on the PCB 212. For example, in some embodiments, the PCB 212 also includes one or more of an accelerometer, a gyroscope, or a magnetometer. For example, in some embodiments, the PCB 212 comprises a chip that includes a three-axis accelerometer, a gyroscope, and magnetometer.

As shown in FIG. 2C, the PCB 212 can include a power source 228 mounted thereon. In some embodiments, for example, as illustrated, the power source 228 is removably mounted on the PCB 212. In the illustrated embodiment, the power source 228 comprises a coin battery removably mounted on the PCB 212. In other embodiments, the power source 228 may be fixedly mounted on the PCB 212. In such embodiments, the power source 228 is preferably rechargeable. The power source 228 is electrically coupled with the one or more sensors to provide power therefore. The power source 228 can be electrically coupled with other electronic components on the PCB 212 as well, such as a processor (e.g., a microprocessor), a data storage module and/or a communication module. The data storage module may be configured to store, for example, firmware for controlling operation of the electronic components of the smart hinge assembly 200 and/or data collected from the one or more sensors. The communications module may be configured to communicate with outside devices to, for example, send the data collected by the one or more sensors or information derived therefrom to the outside device. In some embodiments, the communications module comprises a Bluetooth module, although other communications modules may also be used.

FIGS. 2C and 2D (as well as the cross-sectional view of FIG. 2E) illustrate that the PCB 212 can be positioned between the cover 210 and a gasket 214. Together, the cover 210 and the gasket 214 can be configured to form a recess or space for receiving PCB 212. In some embodiments, the cover 210 and the gasket 214 form a substantially water resistant or water proof enclosure configured to protect the PCB 212. As best seen in FIG. 2C, the gasket 214 can comprise an outer wall 246 that partially or fully laterally surrounds the PCB 212. As best seen in FIG. 2D, the cover 210 can comprise an inner shroud 224 that extends downwardly from an inner surface of the cover 210 to partially or fully laterally surrounds the PCB 212. The outer wall 246 of the gasket 214 and the inner shroud 224 of the cover 210 may cooperate to form the recess or opening that receives the PCB 212.

As shown in FIGS. 2C and 2D, the first bar 202 may form a part of a first or upper geared arm assembly 218, and the second bar 204 may form part of a second or lower geared arm assembly 220. An example of a generic geared arm assembly (referred to using the reference numeral associated with the first geared arm assembly 218), is shown in FIGS. 3A-3G, which are descried in more detail below. With reference to FIGS. 2C-2D, however, some features of the first geared arm assembly 218 and the second geared arm assembly 220 will now be described.

As shown, the first geared arm assembly 218 comprises a first gear 232, the first bar 202, and the insert 206. The first gear 232 may comprise a section including a plurality of gear teeth. As seen in FIG. 2D, an end of the first bar 202 can be coupled to the first gear 232. In particular, and as will be described in more detail below, the end of the first bar 202 that engages the first gear 232 can be countersunk or otherwise positioned within a corresponding recess formed in the first gear 232. This can reduce the overall thickness of the assembly and mechanically couple the first bar 202 to the first gear 232 such that the two rotate together. Similarly, the second geared arm assembly 220 comprises a second gear 234, the second bar 204, and the insert 208. The second gear 234 may comprise a section including a plurality of gear teeth. As seen in FIG. 2D, an end of the second bar 204 can be coupled to the second gear 234. In particular, and as will be described in more detail below, the end of the second bar 204 that engages the second gear 234 can be countersunk or otherwise positioned within a corresponding recess formed in the second gear 324. This can reduce the overall thickness of the assembly and mechanically couple the second bar 204 to the second gear 234 such that the two rotate together.

The gear teeth of the first gear 232 can be meshingly engaged with the gear teeth of the second gear 234. This arrangement can constrain rotational movement of the first gear 232 and the first bar 202 to rotational movement of the second gear 234 and the second bar 204. That is, rotation of the one of the first gear 232 and the first bar 202 or the second gear 234 and the second bar 204 causes a corresponding rotation of the other. In the illustrated embodiment, the first gear 232 and the first bar 202 rotate about the first axis 238 and the second gear and the second bar 204 rotate about a second axis 240. The first and the second axes 238, 240 can be parallel.

As shown in FIG. 2C, in the illustrated embodiment, the second gear 234 comprises a keyed opening 235. The keyed opening 235 can be configured to engage with the drive key 230 to rotationally couple the drive key 230 to the second gear 234 and second bar 204. In this way, rotational motion of the second bar 204 is transferred to the potentiometer 226 and used to adjust the output thereof, providing data from which information about the motion of the knee can be determined.

The first gear 232 and inset end of the first bar 202 and the second gear 232 and inset end of the second bar 204 can be positioned between the hinge plate 216 and the condyle 222. For example, the first gear 232 and inset end of the first bar 202 and the second gear 232 and inset end of the second bar 204 can be positioned between the hinge plate 216 and the condyle 222. The hinge plate 216 (and in some embodiments also the condyle 222) can be sufficiently rigid to support and orient the various components of the smart hinge assembly 200 attached thereto. Attachment of the various components is best visualized in the cross-sectional view of FIG. 2E.

In the cross-sectional view of FIG. 2E, one can see the PCB 212, including the potentiometer 226 and power source 228 positioned between the cover 210 and the gasket 214. Fasteners 241, such as bolts, extend through the cover 210 and the gasket 214 to engage with the hinge plate 216, securing these components to the hinge plate 216. One can also see the first gear 232 (with an end of the first bar 202 nested therein) and the second gear 234 (with an end of the second bar 204 nested therein) positioned between the hinge plate 216 and the condyle 222. In the illustrated embodiment, a rivet 244 extends through the hinge plate 216, the first gear 232, the nested end of the first bar 202, and the condyle 222 to couple these components. The rivet 244, however, does not prevent rotation of the first gear 232 and first bar 202. The drive key 230 and a fastener 242, such as a bolt, extend through the hinge plate 216, the second gear 234, the nested end of the first bar 204, and the condyle 222 to couple these components. As shown, in the illustrated embodiment, the fastener 242 is received within a threaded end of the drive key 230.

The smart hinge assembly 200 can be configured to provide excellent fit and comfort while maintaining the ability to collect accurate data related to the motion of the limb and/or joint, and/or to maintain a low profile. In some embodiments, one or both of these purposes are achieved or facilitated by features related to the first geared arm assembly 218 and the second geared arm assembly 220. In particular, the first bar 202 and the second bar 204 can be configured so that they are very flexible in a frontal plane so as to provide body conforming, comfort, and/or a low profile, while being very stiff in a sagittal plane so as to provide accurate data related to the motion of the limb and/or joint. Additionally, in some embodiments, the ends of the first and second bars 202, 204 can be countersunk within recesses of corresponding first and second gears 232, 234. Countersinking the ends of the first and second bars 202, 204 bars within the corresponding first and second gears 232, 234 can minimize the overall thickness of the smart hinge assembly 200, providing a low profile, and/or facilitate a rigid connection between the bars 202, 204 and the gears 232, 234, facilitating overall stiffness in the sagittal plane.

Examples of these features will be described in more detail with reference to FIGS. 3A-3G, which illustrate a generic geared arm assembly that can be representative of either the first geared arm assembly 218 or the second geared arm assembly 220. In FIGS. 3A-3G, the reference numerals associated with the first geared arm assembly 218 will be used with the understanding that the description is equally applicable to the corresponding components of the second geared arm assembly 220.

Figure 3A:
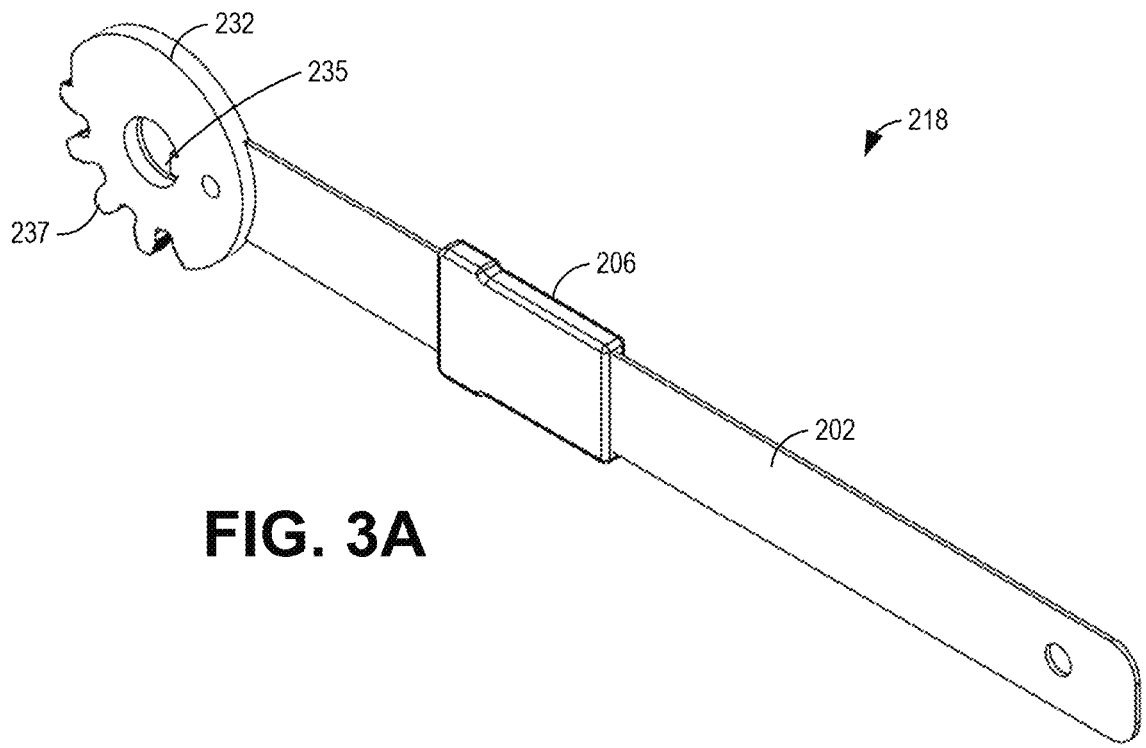
FIG. 3A is a first perspective view of an embodiment of the geared arm assembly, including a gear and a bar, for a hinge assembly such as the smart hinge assembly or other (non-smart) hinge assemblies.
Figure 3B:
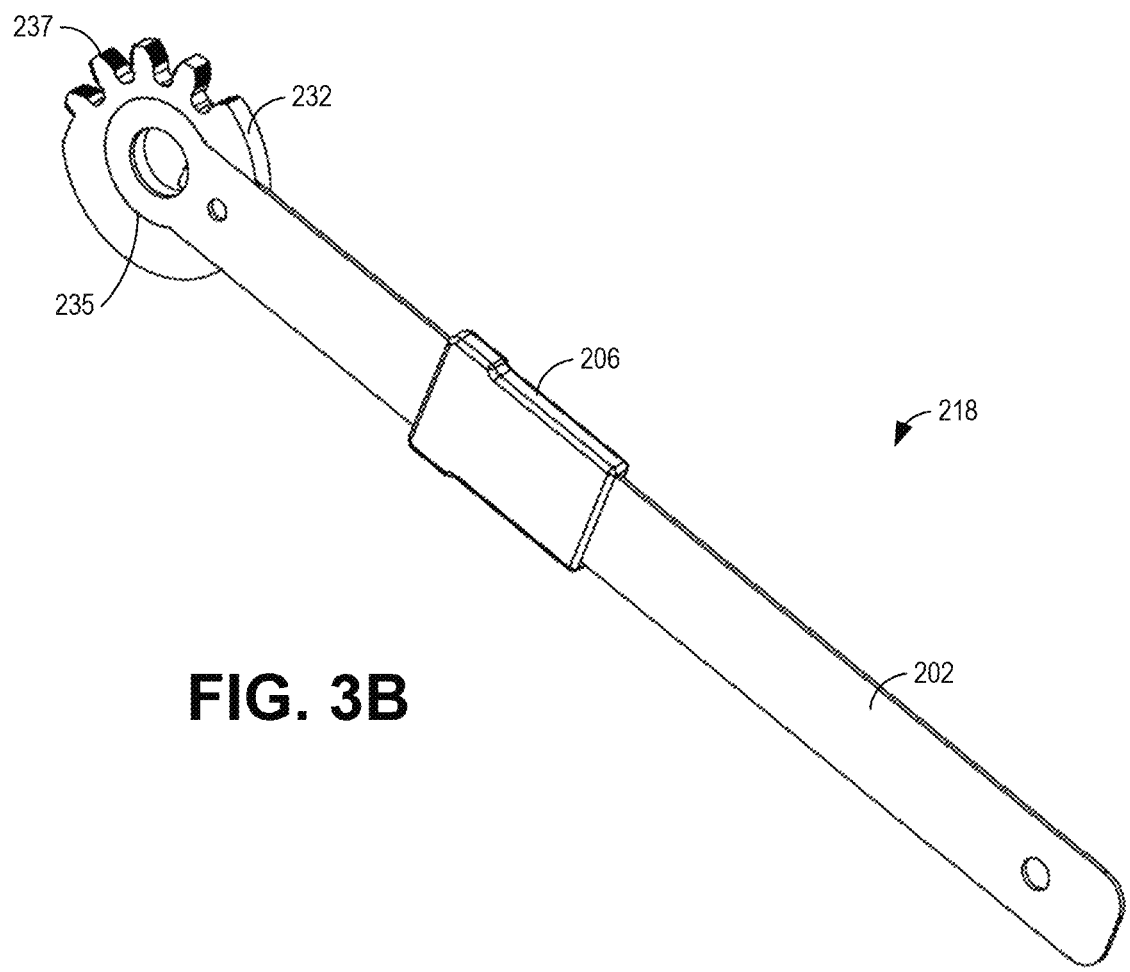
FIG. 3B is a second perspective view of the geared arm assembly.

FIG. 3A is a first perspective view of an embodiment of the geared arm assembly 218, including the gear 232 and the bar 202. The geared arm assembly 218 can be used in the smart hinge assembly 200 described above, or in other hinge assemblies, such as the dummy hinge assembly 300, described below with reference to FIGS. 5A-5D. FIG. 3B is a second perspective view of the geared arm assembly 218, illustrating an opposite side thereof.

As shown in FIGS. 3A and 3B, the bar 202 may extend between a first end and a second end. The first end may be coupled to the gear 232. In the illustrated embodiment, the first end is nested within a recess of the gear 232 such that a rear surface of the bar 202 and the gear 232 is flush (see FIG. 3B). The second end of the bar 202 is free and is configured to inserted into the slot 114 of the upper receptacle 110 (see FIG. 1) as described above. Between the first end and the second end, the insert 206 is positioned on the bar 202. The insert is positioned such that it surrounds the bar 202 at the point that the bar 202 enters the slot 114. As noted previously, the insert 206 can comprise an elastomer or other material overmolded onto the bar 202 configured in size and shape to locate the bar 202 within the slot 114 and provide a tight fit therebetween. The insert 206 can also be configured to distribute contact forces between the bar and the slot 114 over a larger surface area to reduce or prevent wear between the bar 202 and the slot 114. The insert 206 can also be configured elevate the bar 202 slightly above the fabric of the garment 102 to prevent the bar 202 from cutting or puncturing the garment 102. In some embodiments, the insert 206 is configured to extend entirely to the second end of the bar 202.

The gear 232 and the first end of the bar 202 nested therein can be configured with an opening 235 which extends therethrough. The opening 235 can be configured to allow the gear 232 and the first end of the bar 202 to be coupled to the remainder of the smart hinge assembly 200 as described above with reference to FIG. 2E. In some embodiments, for example, as illustrated, the opening 235 comprises a keyed opening having a profile that engages with the drive key 230 to transfer rotational motion between the gear 232 and the bar 202 and the potentiometer 226.

The gear 232 includes a section comprising gear teeth 237. The gear teeth 237 are configured to mesh with corresponding teeth on the opposite gear to constrain rotation motion of the two together.

Figure 3C:
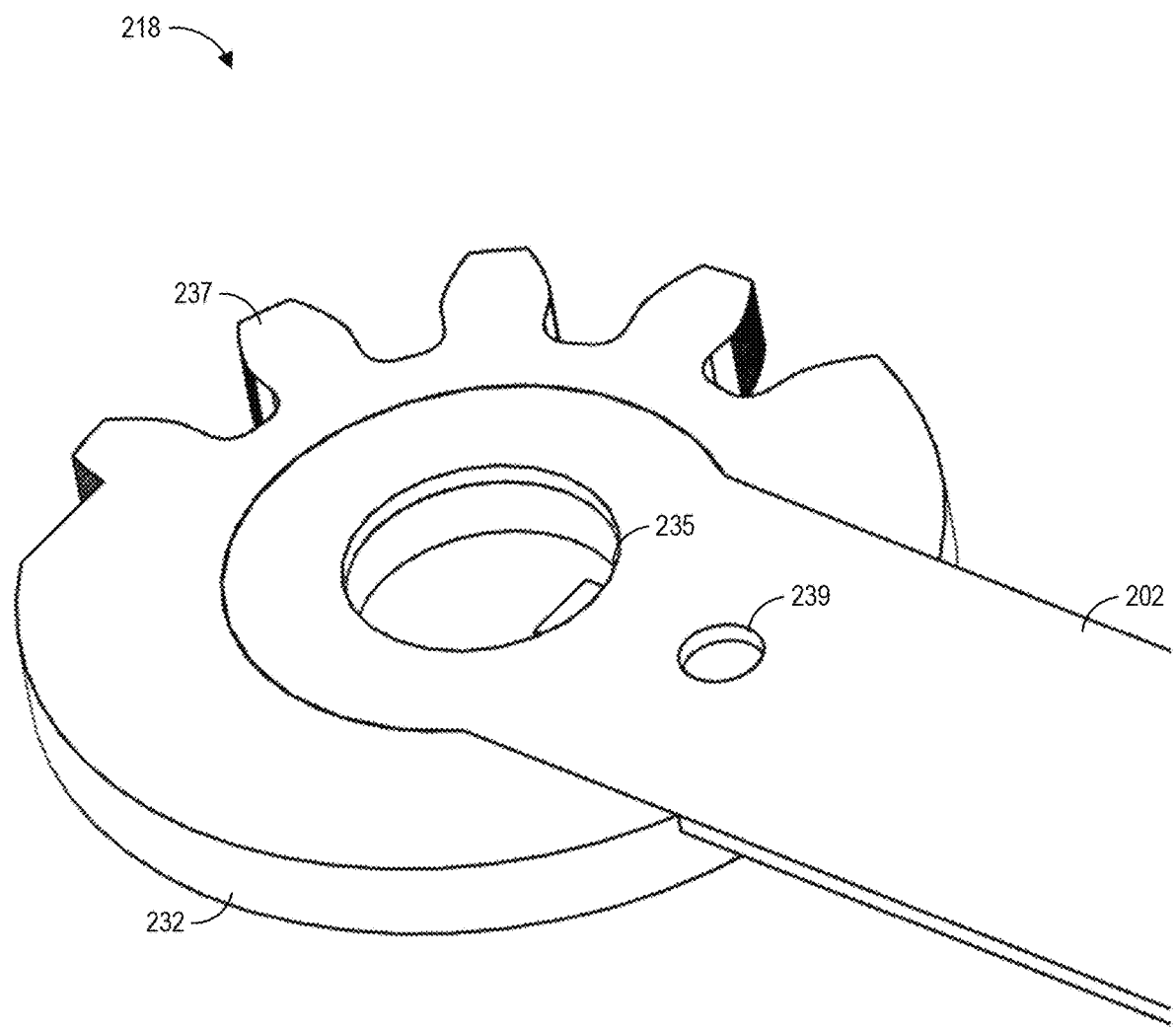
FIG. 3C is a detail view of the geared arm assembly illustrating that an end of the bar can be received within a corresponding recess of the gear.
Figure 3D:
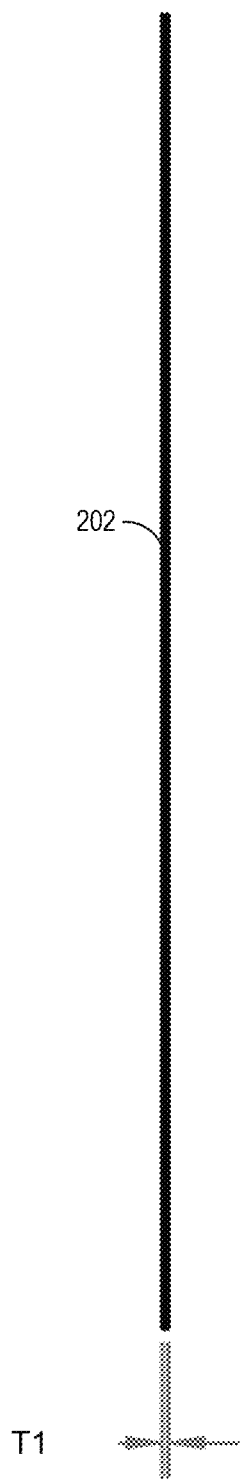
FIG. 3D is a side view of an embodiment of the bar of the geared arm assembly illustrating example dimensions therefor.

FIG. 3C is a detail view of the geared arm assembly 218 illustrating that the first end of the bar 202 can be received within a corresponding recess of the gear 232. As shown in this view, the gear 232 can be thicker than the bar 202. A recess can be formed in the gear having the same size and shape as the first end of the bar 202. The recess can have the same depth as the thickness of the bar 202. When the first end of the bar 202 is positioned within the recess, the surfaces of the gear 232 and the bar 202 can be flush, facilitating the overall low profile of the hinge assembly. Further, the corresponding shapes of the recess of the gear 232 and the first end of the bar 202 can cause the first end of the bar 202 to be closely received within the recess, such that any play between the two is eliminated or nearly eliminated. This can ensure that rotation of the bar 202 is transferred directly and accurately to rotation of the gear 232, helping to ensure that data collected by the potentiometer 226 is highly accurate. As shown in FIG. 3c, in some embodiments, a pin 239 can be inserted through the bar and the gear 232 to further connect the two.

Figure 3E:
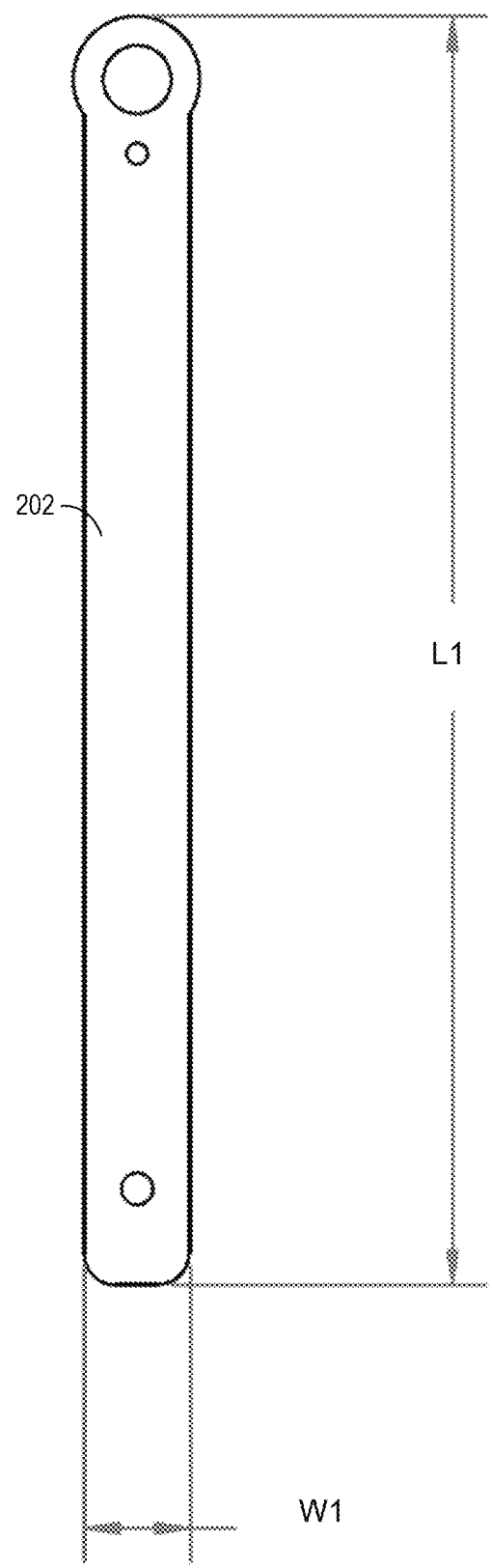
FIG. 3E is a top view of the bar illustrating example dimensions therefor.

As noted above, the bar 202 can be configured to be very flexible in a frontal plane so as to provide body conforming, comfort, and/or a low profile, while being very stiff in a sagittal plane so as to provide accurate data related to the motion of the limb and/or joint. This can be accomplished through the dimensions of the bar 202 as well as the material from which the bar 202 is made. FIGS. 3D and 3E illustrate example dimensions for the bar 202. As shown in FIG. 3D, the bar 202 may comprise a thickness T1. In general, the thickness is selected such that the bar 202 is very flexible in a frontal plane so as to allow the bar 202 to conform to the shape of the user's leg. In some embodiments, the thickness T1 may be about, equal to, or less than 1 mm, 0.9 mm, 0.8 mm, 0.75 mm, 0.7 mm, 0.6 mm, 0.5 mm, 0.4 mm, 0.3 mm, 0.25 mm, or thinner. As shown in FIG. 3E, the bar 202 may comprise a width W1. In general, the width W1 is selected so that the bar 202 is very stiff in the sagittal plane such that any motion of the bar 202 in the sagittal plane is due to rotation of the bar 202, rather than bending of the bar 202 in the sagittal plane. The width W1 of the bar 202 may be about, equal to, or greater than 2.5 mm, 3 mm, 4 mm, 5 mm, 6 mm, 7.5 mm, 8 mm, 9 mm, 10 mm, 11 mm, 12, mm 14 mm, 15 mm or greater. In general, the thickness T1 should be selected so as to be much smaller than the width W1, such that the bar 202 is flexible in the frontal plane and stiff in the sagittal plane. For example, in some embodiments, the width W1 is at least 5×, 10×, 15×, 20×, larger than the thickness T1.

FIG. 3E also illustrates an example length dimensions L1 for the bar 202. The bar 202 should be sufficiently long so as to extend from a region over the knee joint to a region above or below the knee joint so as to couple the region above or below the knee joint to the hinge. For example, the length L1 may be at least, about, or greater than 80 mm, 90 mm, 100 mm, 110 mm, 120 mm, 130 mm, 140 mm, 150 mm or greater.

In one example, the bar 202 has a thickness T1 of about 0.5 mm, a width W1 of about 10 mm, and a length L1 of about 120 mm.

The bar 202 may comprise spring steel or other suitable or similar materials. Use of spring steel or other suitable or similar materials in conjunction with the described dimensions provides flexibility in the frontal plan and rigidity in the sagittal plane.

Figure 3F:
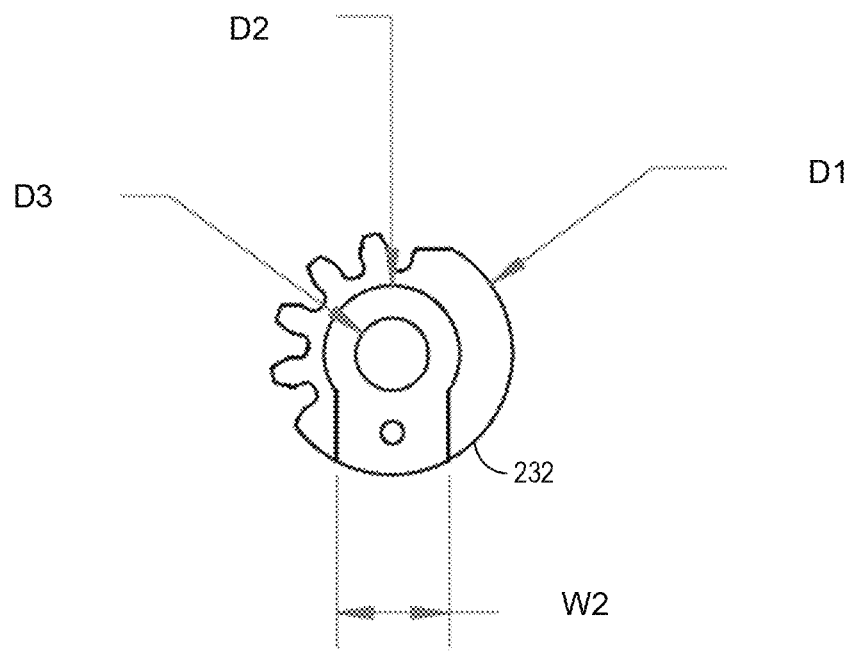
FIG. 3F is a top view of an embodiment of the gear of the geared arm assembly illustrating example dimensions therefor.
Figure 3G:
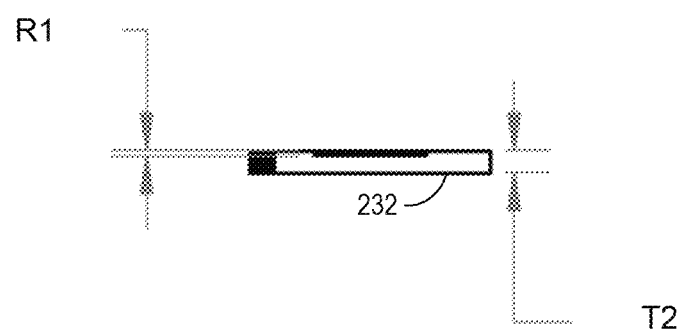
FIG. 3G is a side view of the gear illustrating example dimensions therefor.

FIGS. 3F and 3G illustrate example dimensions for the gear 232 including dimensions for the recess thereof. As noted above, the dimensions of the recess are generally selected so as to very closely correspond with or match the dimensions of the end of the bar 202. As shown in FIG. 3F, the gear 232 may comprise an outer diameter D1, an inner diameter D2 (related to shape of the recess), and an opening dimeter D3. In some embodiments, the outer diameter D1 is about 18 mm, about 20 mm, about 21 mm, about 21.5 mm, about 22 mm, or about 24 mm, although other sizes are also possible. The inner diameter D2 defining a portion of the recess may be, for example, about 8 mm, about 10 mm, about 12 mm, about 14 mm, although other sizes are also possible. In some embodiments the inner dimeter D2 is greater than the width W1 of the bar. A width dimension W2 as illustrated also defines a portion of the recess. The width dimension W2 can be selected to correspond to the width W1 of the bar 202. The inner diameter D3 can be, for example, about 5 mm, about 6 mm, about 6.5 mm, about 7 mm, or about 8 mm, although other sizes are also possible.

FIG. 3F illustrates that the gear 232 may comprise a thickness T2 and recess depth R1. In some embodiments, the thickness T2 is at least, about, exactly, or at most 1 mm, 2 mm, 3 mm, or 4 mm, although other thicknesses are possible. In general the thickness T2 is greater than the thickness T1 of the bar 202. The recess depth R1 can be selected to correspond to the thickness T1 of the bar 202 such that when the bar 202 is nested within the recess, outer surfaces of the bar 202 and the gear 232 are flush.

Figure 4A:
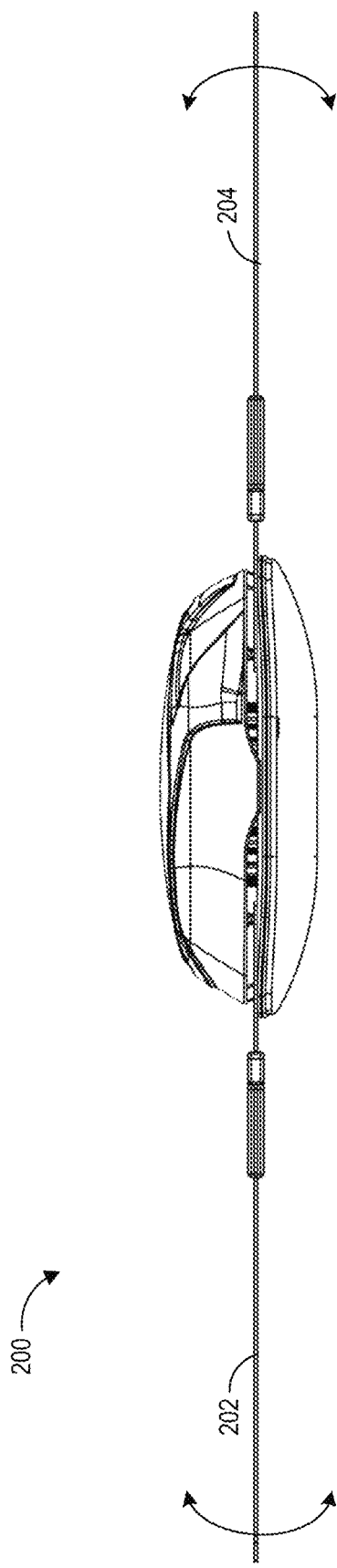
FIG. 4A is a side view of the smart hinge assembly of FIG. 1 illustrating that the bars of the geared arm assemblies are flexible in a frontal plane.
Figure 4B:
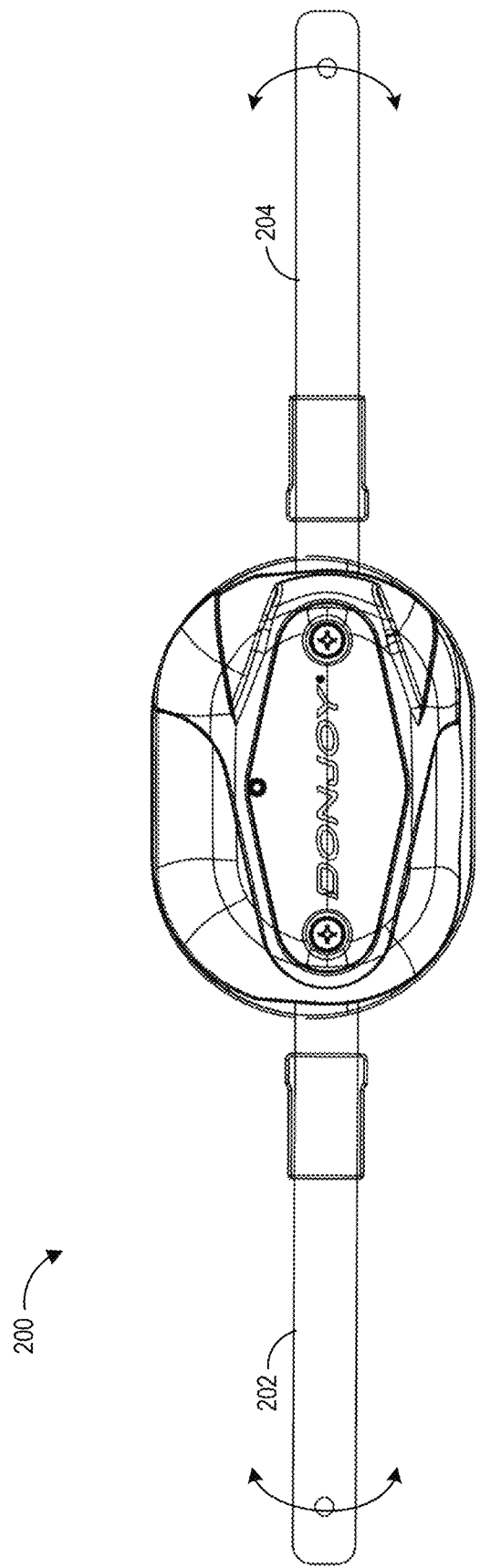
FIG. 4B is a top view of the smart hinge assembly of FIG. 1 illustrating that the bars of the geared arm assemblies are stiff in a sagittal plane.

FIGS. 4A and 4B are side and top views, respectively of the hinge assembly 200 and are used to illustrate how the bars 202, 204 are flexible in the frontal plane and stiff in the sagittal plane. In particular, the bars 202, 204 such that they are highly flexible within the frontal plane. As shown in FIG. 4A, the bars 202, 204 can easily flex backwards and forwards in the directions of the illustrated arrows due to the thinness of the bars 202, 204 in this direction. This flexibility allows for a comfortable fit of the bars 202, 204 to the side of the leg. In contrast, the bars 202, 204 are rigid in the sagittal plane. As shown in FIG. 4B, the bars 202 are resistant to flexing the directions of the illustrated arrows, owing to their width in this direction. Rather, motion of the bars 202, 204 in the direction of the arrows of FIG. 4B is caused by rotation of the bars 202, 204 due to flexion or extension of the knee. This improves the ability of the smart hinge assembly 200 to capture accurate data regarding the motion of the knee.

FIGS. 5A-5D relate to another embodiment of a hinge assembly 300. In many respects the hinge assembly 300 is similar to the hinge assembly 200. In particular, the hinge assembly 300 can be similarly configured so as to be flexible in the frontal plane and stiff in the sagittal plane and to have an overall low profile. In contrast with the hinge assembly 300, the hinge assembly 200 does not include any sensors or electronic components. Accordingly, the hinge assembly 300 may be considered a dummy hinge or a non-smart hinge. By not including the sensors and electronic components, the hinge assembly 300 may be thinner even than the smart hinge assembly 200.

Figure 5A:
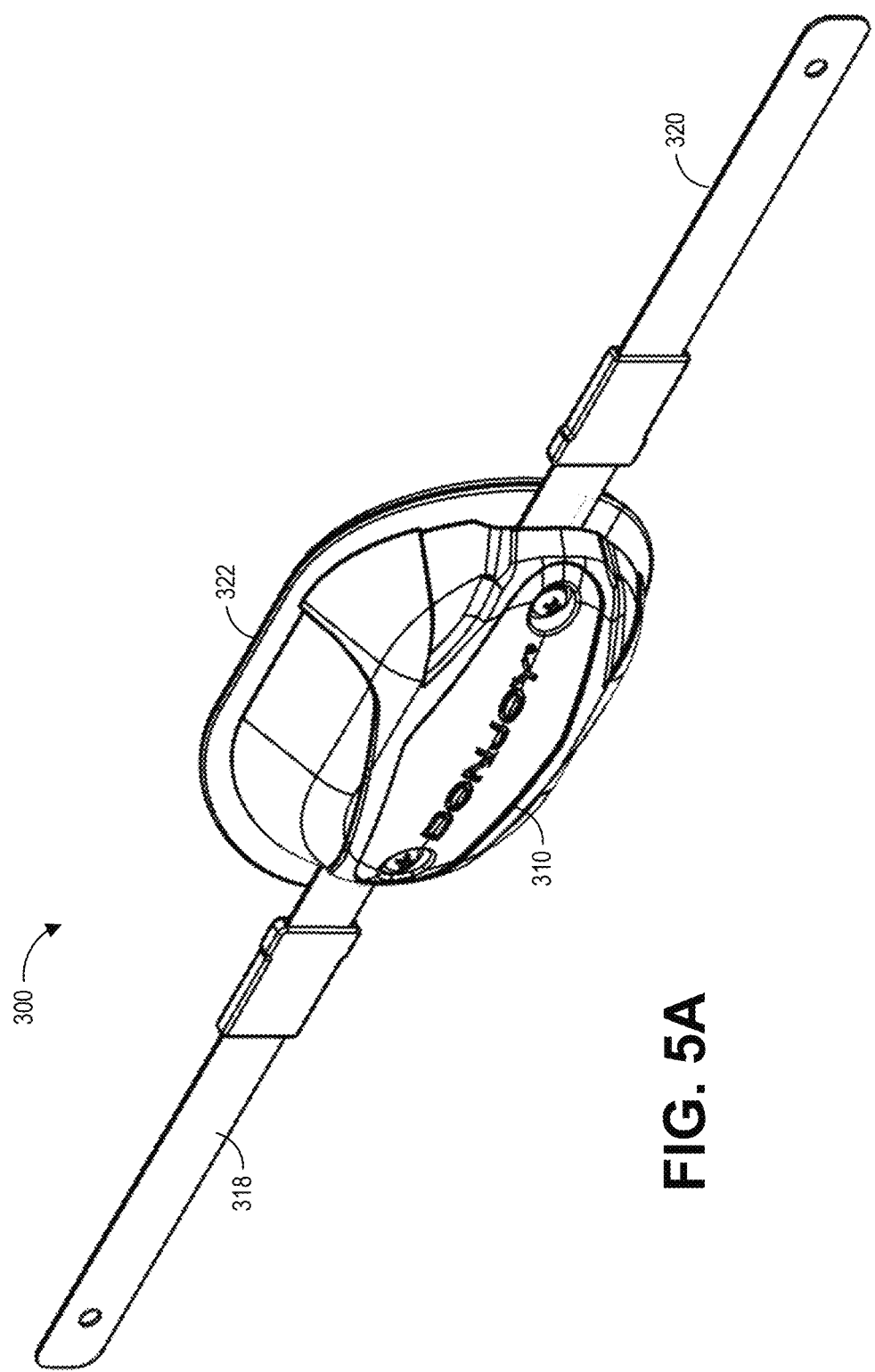
FIG. 5A is a perspective view of an embodiment another hinge assembly.
Figure 5B:
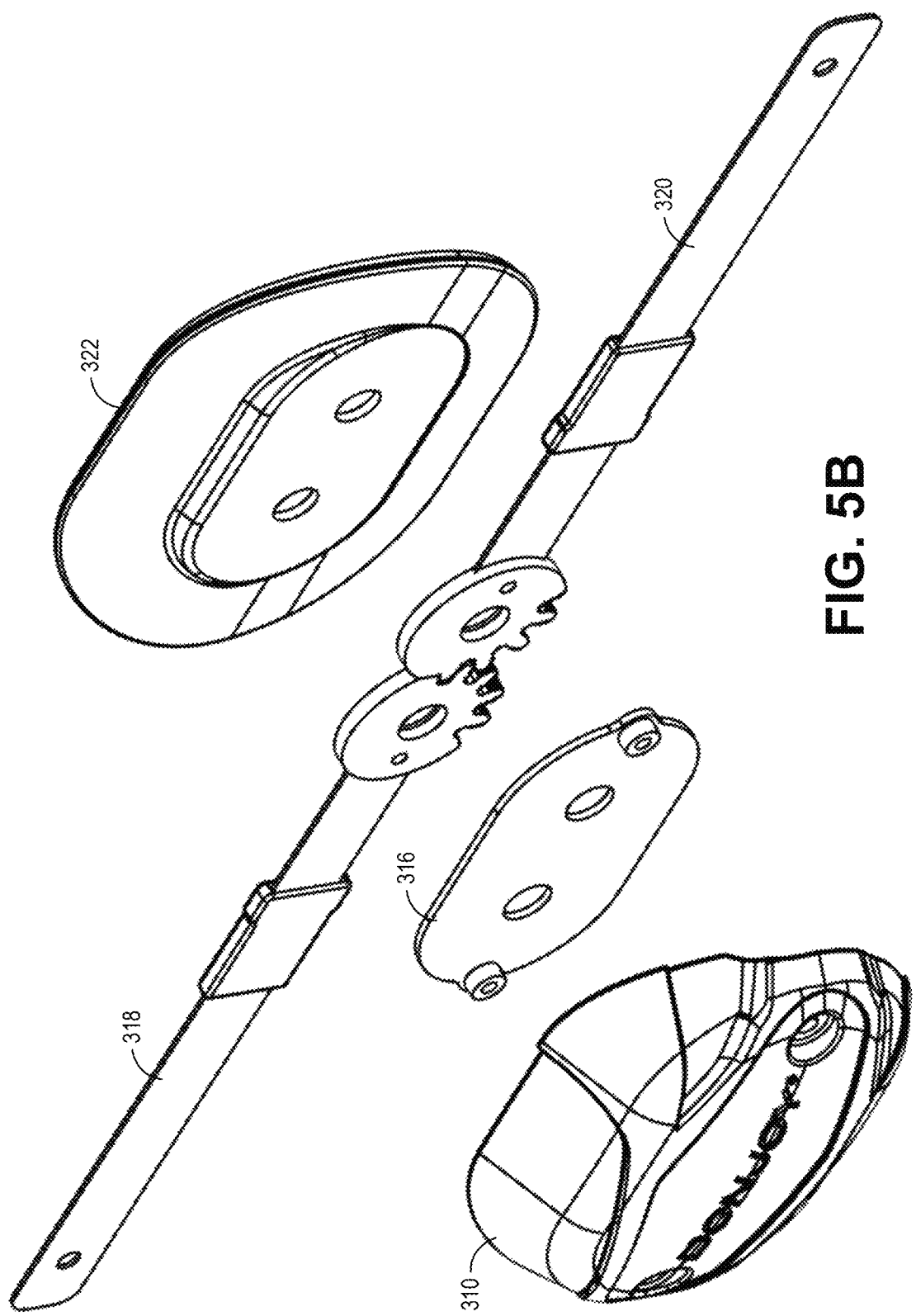
FIG. 5B is a first exploded perspective view of the hinge assembly of FIG. 5A.
Figure 5C:
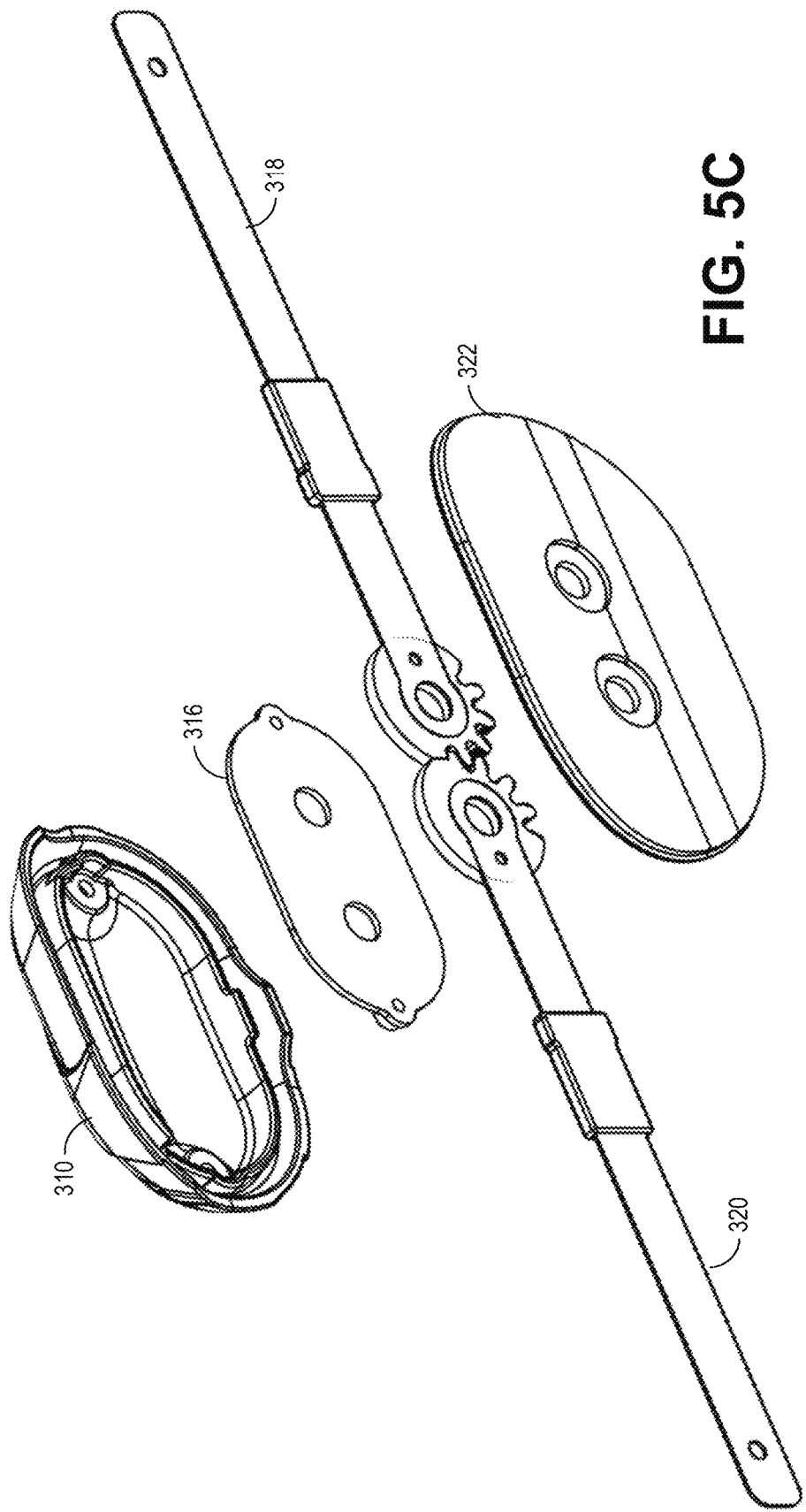
FIG. 5C is a second exploded perspective view of the hinge assembly of FIG. 5A.
Figure 5D:
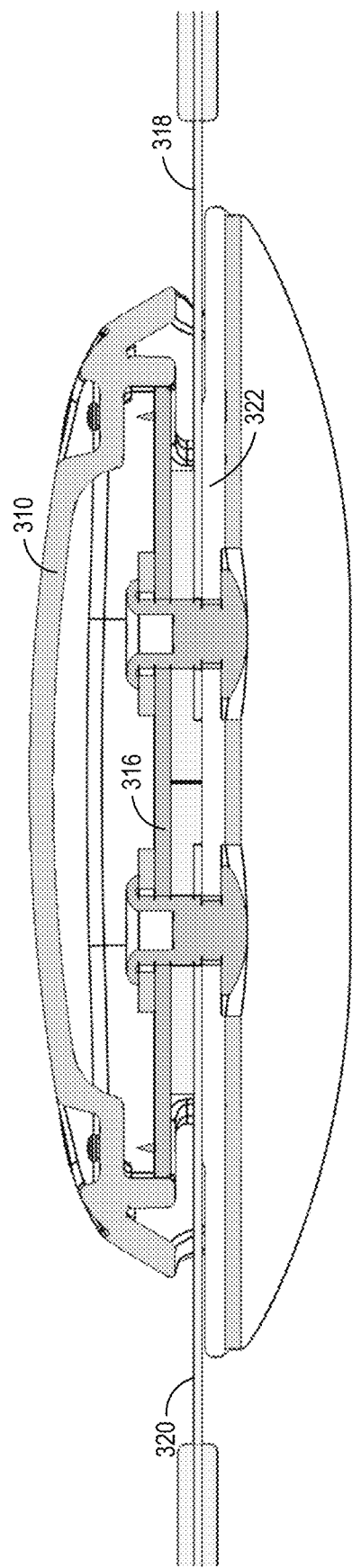
FIG. 5D is a cross-sectional view of the hinge assembly of FIG. 5A taken through a sagittal plane.

FIG. 5A is a perspective view, FIG. 5B is a first exploded perspective view, FIG. 5C is a second exploded perspective view, and FIG. 5D is a cross-sectional view of the hinge assembly 300 taken through a sagittal plane. As shown in these figures, the hinge assembly 300 includes a cover 310, a hinge plate 316, first and second geared arm assemblies 318, 320, and a condyle 322. In comparison to the smart hinge assembly 200, the PCB 212, electronic components, and gasket 214 are omitted in the hinge assembly 300, allowing for the hinge assembly 300 to be thinner than the hinge assembly 200. The remaining components are generally similar to corresponding components of the smart hinge assembly 200 and accordingly are not described here with the understanding the preceding description is applicable.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A smart brace comprising:
   a flexible compressive garment configured to be worn on a limb over a joint, the flexible compressive garment consisting of:
      a sleeve consisting of a single continuous loop of material,
      a rigid molded upper receptacle fixedly attached to an upper portion of the sleeve, and
      a rigid molded lower receptacle fixedly attached to a lower portion of the sleeve; and
   a smart hinge removably coupled to the flexible compressive garment, the smart hinge comprising:
   a first bar at least partially received within the rigid molded upper receptacle of the flexible compressive garment above the joint, the first bar having a thickness less than about 0.5 mm and a width greater than or equal to about 5.0 mm, and wherein the first bar is configured to rotate about a first axis with flexion or extension of the joint,
      wherein the rigid molded upper receptacle comprises an upper slot that removably receives a second end of the first bar to couple the first bar to the upper portion, and
      wherein the first bar comprises a first insert overmolded on the first bar between a first end and the second end, the first insert configured to engage with the upper slot, thereby providing a tight fit between the first bar and the upper slot and distributing contact forces between the first bar and the upper slot over a larger surface area to prevent wear therebetween;
   a second bar at least partially received within the rigid molded lower receptacle of the flexible compressive garment below the joint, the second bar having a thickness less than about 0.5 mm and a width greater than or equal to about 5.0 mm, and wherein the second bar is configured to rotate about a second axis with flexion or extension of the joint,
      wherein the rigid molded lower receptacle comprises a lower slot that removably receives a second end of the second bar to couple the second bar to the lower portion, and
      wherein the second bar comprises a second insert overmolded on the second bar between a first end and the second end, the second insert configured to engage with the lower slot, thereby providing a tight fit between the second bar and the lower slot and distributing contact forces between the second bar and the lower slot over a larger surface area to prevent wear therebetween; and
   at least one potentiometer comprising a rotatable component that is rotationally coupled to the first bar or the second bar by way of a drive key;
   wherein the first bar and the second bar are flexible in a frontal plane such that the first bar and the second bar are configured to be body conforming and low profile and rigid in a sagittal plane such that the first bar and the second bar are configured to accurately gather data related to motion of the joint.

2. The smart brace of claim 1, wherein the smart hinge is coupled to the flexible compressive garment on a lateral side, and the smart brace further comprises a dummy hinge assembly coupled to the flexible compressive garment on a medial side.

3. The smart brace of claim 2, wherein the dummy hinge assembly comprises:
   a first bar coupled to an upper portion of the flexible compressive garment above the joint, the first bar configured to rotate about a first axis with flexion or extension of the joint; and
   a second bar coupled to a lower portion of the flexible compressive garment below the joint, the second bar configured to rotate about a second axis with flexion or extension of the joint;
   wherein the first bar and the second bar are flexible in a frontal plane and rigid in a sagittal plane.

4. The smart brace of claim 1, wherein each of the first bar and the second bar comprise spring steel.

5. The smart brace of claim 1, wherein:
   the first end of the first bar is countersunk within a first gear; and
   the first end of the second bar is countersunk within a second gear, the second gear meshingly engaged with the first gear such that rotation of the first bar about the first axis causes a corresponding rotation of the second bar about the second axis.

6. The smart brace of claim 1, wherein the joint comprises a knee.

7. A low-profile hinge assembly for a smart brace, the hinge assembly comprising:
   a first geared arm assembly comprising a first gear and a first bar, a first end of the first bar received flush within a recess of the first gear, wherein the recess of the first gear is identical in size and shape as the first end of the first bar;
   a second geared arm assembly comprising a second gear and a second bar, a first end of the second bar received flush within a recess of the second gear, wherein the recess of the second gear is identical in size and shape as the first end of the second bar; and
   a hinge plate, the first geared arm assembly connected to the hinge plate for rotation about a first axis and the second geared arm assembly connected to the hinge plate for rotation about a second axis, and the first gear meshingly engaged with the second gear such that rotation of the first geared arm assembly causes a corresponding rotation of the second geared arm assembly;
   wherein the hinge plate is coupled with at least one potentiometer comprising a rotatable component that is rotationally coupled to the first bar or the second bar by way of a drive key, the at least one potentiometer configured to gather data related to motion of a joint, and wherein the end of one of the first bar or the second bar comprises a keyed opening, the drive key engaged with the keyed opening to couple the potentiometer to the end of the one of the first bar or the second bar such that rotation of the one of the first bar or the second bar about the corresponding first or second axis adjusts an output of the potentiometer;

wherein the first bar and the second bar each have a thickness less than about 0.5 mm and a width greater than or equal to about 5.0 mm, and wherein the first bar and the second bar are flexible in a frontal plane such that the first bar and the second bar are configured to be body conforming and low profile and rigid in a sagittal plane such that the first bar and the second bar are configured to accurately gather data related to motion of the joint; and wherein the low-profile hinge assembly is configured to be removably coupled to a flexible compressive garment, the flexible compressive garment consisting of:
  a sleeve consisting of a single continuous loop of material,
  a rigid molded upper receptacle fixedly attached to an upper portion of the sleeve, and
  a rigid molded lower receptacle fixedly attached to a lower portion of the sleeve, wherein the first bar comprises an insert overmolded on the first bar between the first end and a second end of the first bar, the insert configured to engage with an upper slot that removably receives the second end of the first bar to couple the first bar to the upper portion of the sleeve, thereby providing a tight fit between the first bar and the upper slot and distributing contact forces between the first bar and the upper slot over a larger surface area to prevent wear therebetween, and wherein the second bar comprises an insert overmolded on the second bar between the first end and a second end of the second bar, the insert configured to engage with a lower slot that removably receives the second end of the second bar to couple the second bar to the lower portion of the sleeve, thereby providing a tight fit between the second bar and the lower slot and distributing contact forces between the second bar and the lower slot over a larger surface area to prevent wear therebetween.

8. The hinge assembly of claim 7, further comprising:
at least one sensor configured to gather data related to motion of at least one of the first and second geared arm assemblies; and a power source electrically coupled to the at least one sensor.

9. The hinge assembly of claim 8, wherein the at least one sensor and the power source are positioned on a printed circuit board, and the hinge assembly further comprises:
  a gasket that at least partially receives the printed circuit board; and
  a cover that covers the gasket and the printed circuit board, wherein the gasket and cover define a water resistant recess in which the printed circuit board is positioned.

10. The hinge assembly of claim 9, wherein:
the hinge plate, the gasket, the printed circuit board, and the cover are positioned on a first side of the first and second geared arms;
a condyle is positioned on a second side of the first and second geared arms; and during use of a smart brace including the hinge assembly, the first side is positioned away from a wearer and the second side is positioned toward the wearer.

11. The hinge assembly of claim 7, wherein the recess of each of the first and second gears comprises a shape that corresponds to a shape of the end of the corresponding first and second bars, such that the end of each of the first and second bars is closely received within the corresponding recess of the first and second gears.

12. The hinge assembly of claim 11, wherein the recess of each of the first and second gears is configured such that the corresponding first and second bars is countersunk within the corresponding recess of the first and second gears.

13. The hinge assembly of claim 7, wherein each of the first bar and the second bar comprise:
  a width greater than or equal to about 7.5 mm providing rigidity in the sagittal plane.

14. The hinge assembly of claim 7, wherein each of the first bar and the second bar comprise spring steel.

* * * * *